(12) United States Patent
Santiago et al.

(10) Patent No.: US 10,830,732 B2
(45) Date of Patent: *Nov. 10, 2020

(54) CONTROL OF CHEMICAL REACTIONS USING ISOTACHOPHORESIS

(71) Applicant: The Board of Trustees of the Leland Stanford Junior University, Palo Alto, CA (US)

(72) Inventors: Juan G. Santiago, Stanford, CA (US); Alexandre Persat, Princeton, NJ (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/121,219

(22) Filed: Sep. 4, 2018

(65) Prior Publication Data
US 2018/0372682 A1    Dec. 27, 2018

Related U.S. Application Data

(60) Continuation of application No. 15/081,415, filed on Mar. 25, 2016, now Pat. No. 10,073,054, which is a
(Continued)

(51) Int. Cl.
*G01N 27/447* (2006.01)
*C12Q 1/686* (2018.01)
(Continued)

(52) U.S. Cl.
CPC ....... *G01N 27/44765* (2013.01); *B01D 57/02* (2013.01); *C12M 1/42* (2013.01);
(Continued)

(58) Field of Classification Search
CPC .......... G01N 27/447; G01N 27/44704; G01N 27/44756; G01N 27/44791
See application file for complete search history.

(56) References Cited

U.S. PATENT DOCUMENTS 5,817,225 A    10/1998  Hinton
5,939,291 A     8/1999  Loewy et al.
(Continued)

FOREIGN PATENT DOCUMENTS

WO    WO2005/033283    4/2005

OTHER PUBLICATIONS

Routs, R. J. (1971). Electrolyte systems in isotachophoresis and their applications to some protein separations Eindhoven:Technische Hogeschool Eindhoven DOI: 10.6100/IR43649 (Year: 1971).*
(Continued)

*Primary Examiner* — Alexander S Noguerola
(74) *Attorney, Agent, or Firm* — Lumen Patent Firm

(57) ABSTRACT

Isotachophoresis (ITP) is exploited to control various aspects of chemical reactions. In a first aspect, at least one of the reactants of a chemical reaction is confined to an ITP zone, but the resulting product of the chemical reaction is separated from this ITP zone by the ITP process. In a second aspect, one or more reactants of a chemical reaction are confined to an ITP zone, and one or more other reactants of the chemical reaction are not confined to this ITP zone. In a third aspect, ITP is employed to confine at least one reactant of a chemical reaction to an ITP zone, and at least one reactant of the chemical reaction is delivered to the ITP zone in two or more discrete doses. These aspects are especially relevant to performing polymerase chain reactions using chemical denaturants as opposed to thermal cycling.

34 Claims, 5 Drawing Sheets

Related U.S. Application Data continuation of application No. 14/465,138, filed on Aug. 21, 2014, now Pat. No. 9,297,039, which is a continuation of application No. 13/764,376, filed on Feb. 11, 2013, now Pat. No. 8,821,704, which is a division of application No. 12/587,537, filed on Oct. 7, 2009, now Pat. No. 8,394,251.

(60) Provisional application No. 61/195,395, filed on Oct. 7, 2008.

(51) Int. Cl.
  *C12M 1/42* (2006.01)
  *B01D 57/02* (2006.01)
  *C12P 19/34* (2006.01)

(52) U.S. Cl.
  CPC .............. *C12P 19/34* (2013.01); *C12Q 1/686* (2013.01); *G01N 27/447* (2013.01); *G01N 27/44721* (2013.01); *G01N 27/44795* (2013.01); *C12Q 2565/125* (2013.01); *G01N 27/44791* (2013.01)

(56) References Cited

U.S. PATENT DOCUMENTS

| | | |
|---|---|---|
| 10,073,054 B2* | 9/2018 | Santiago .............. C12Q 1/686 |
| 2004/0058349 A1 | 3/2004 | van Ness et al. |
| 2005/0115837 A1 | 6/2005 | Burgi et al. |
| 2008/0000774 A1 | 1/2008 | Park et al. |
| 2008/0020386 A1 | 1/2008 | Chen et al. |
| 2008/0166770 A1 | 7/2008 | Morita et al. |

OTHER PUBLICATIONS

Kuhn et al., "Free flow electrophoresis as a method for the purification of enzymes from *E. coli* cell extract," Electrophoresis 1989, 10, 165-172 (Year: 1989).*

Cui et al., "Isotachophoressis of proteins in a networked microfliudc chip: Experiement and 2-D simulation," Electrophoresis 2007, 26, 1138-1146 (Year: 2007).*

Article entitled "Denaturing Polyacrylamide Gel Electrophoresis of DNA & RNA" from the National Diagnostics website https://www.nationaldiagnostics.com/electrophoresis/article/denaturing-polyacrylamide-gel-electrophoresis-dna-rna (Year: 2019).*

Breadmore, "Unlimited-volume stacking of ions in capillary electrophoresis. Part 1: Stationary isotachophoretic stacking of anions", 2008, Electrophoresis v29, pp. 1082-1091.

Erlich et al., "Recent advances in the polymerase chain reaction", 1991, Science v252, pp. 1643-1651.

Morita et al., "On-chip isothermal polymerase chain reaction", 2007, Proceedings IMECE, IMECE2007-43070.

Thormann et al., "Impact of electroosmosis on isotachophoresis in open-tubular fused-silica capillaries: Analysis of the evolution of a stationary steady-state zone structure by computer simulation and experimental validation", 1995, Electrophoresis v16, pp. 2016-2026.

Zhang et al., "Direct PCR sequencing with denaturants (Formamide)", 1996, In Rapley (eds.) PCR sequencing protocols, methods in molecular biology v65, pp. 137-147.

* cited by examiner

Axial channel distance

CONTROL OF CHEMICAL REACTIONS USING ISOTACHOPHORESIS

CROSS REFERENCE TO RELATED APPLICATIONS

This application is a continuation of U.S. Ser. No. 15/081,415, filed on Mar. 25, 2016, and hereby incorporated by reference in its entirety. Application Ser. No. 15/081,415 is a continuation of U.S. Ser. No. 14/465,138, filed Aug. 21, 2014, and hereby incorporated by reference in its entirety. Application Ser. No. 14/465,138 is a continuation of U.S. Ser. No. 13/764,376 filed Feb. 11, 2013, and hereby incorporated by reference in its entirety. Application Ser. No. 13/764,376 is a divisional of U.S. Ser. No. 12/587,537 filed Oct. 7, 2009, and hereby incorporated by reference in its entirety. Application Ser. No. 12/587,537 claims the benefit of U.S. provisional patent application 61/195,395, filed on Oct. 7, 2008, entitled "Methods and Apparatus for Controlled Chemical Cycling, Isothermal Polymerase Chain Reaction", and hereby incorporated by reference in its entirety.

FIELD OF THE INVENTION

This invention relates to control of chemical reactions.

BACKGROUND

Chemical reactions are frequently controlled in specialized ways in order to provide various benefits, such as improved yield, increased reaction rate, analysis of products, etc. One example of an important reaction that is often subject to specialized control is the polymerase chain reaction (PCR). PCR is itself a multi-reaction process which may include several types of chemical processes including DNA denaturation, primer annealing, primer extension (with the aid of an enzyme), and for real time detection may include side reactions such as hybridization (e.g., with a fluorescently labeled oligonucleotide) or intercalation of a fluorescent molecule into polynucleotide. PCR is an essential tool in both biology and medicine, and is the technique of choice for DNA amplification. It is commonly used for the identification as well as quantification of nucleic acids or polynucleotides, in particular of deoxyribonucleic acid (DNA) and ribonucleic acid (RNA). Exemplary applications are diagnosis of hereditary disease, forensics, gene expression profiling and pathogen detection.

At the present time, most PCR efforts use "thermal cycling". In this method, double-stranded nucleic acid is subjected to a three-step thermal cycle where it is denatured, annealed, and extended by the action of a thermostable DNA polymerase. In a typical thermal cycling process, the reaction temperature is cycled between 55 and 94 degrees Celsius, thus reaching a point where ordinary polymerases typically denature. Conventional thermal PCR requires costly and complex equipment and can be difficult to automate in miniaturized devices. It requires significant instrumentation, thermal control, and an expensive, thermostable DNA polymerase. Attempts have been made to avoid thermal cycling in PCR. For example, chemical denaturation (as opposed to thermal denaturation) is considered in U.S. Pat. No. 5,939,291 and in US 2008/0166770.

Electrokinetic and microfluidic technology have been demonstrated for controlling some aspects of chemical reactions. For example, in US 2008/0000774, several methods for controlling the concentration of chemical reactants in a microfluidic system are considered. Enhancing the concentration of a reactant is often referred to as "focusing" the reactant.

Although it would be attractive to provide for isothermal PCR in a miniaturized fluidic system, conventional fluidic approaches tend to have difficulty with the specialized requirements of PCR (e.g., the large number of reaction cycles, and the need for tight control of reactant and/or product location). Accordingly, it would be an advance in the art to provide improved chemical reaction control, especially in relation to microfluidic PCR.

SUMMARY

In the present approach, isotachophoresis (ITP) is exploited to control various aspects of chemical reactions. In ITP, a sample of one or more analytes is typically introduced between a leading electrolyte (LE, containing a leading ion) and a trailing electrolyte (TE, containing a trailing ion). The leading ion, trailing ion and sample components all have the same charge polarity, (i.e., are all anions or cations). Typically, the sample components have effective electrophoretic mobility less than that of the leading ion, but greater than that of the trailing ion. Initially, the sample can be mixed with the LE, with the TE, between the LE and TE, or with both the LE and TE. On application of an electric potential to this system, sample components migrate toward the region between the LE and TE. Typically, these sample ions then form discrete contiguous zones of analyte arranged in order of their (effective) electrophoretic mobilities with the highest mobility nearest the LE. Further details relating to isotachophoresis are described in a text "Isotachophoresis: theory, instrumentation, and applications" by authors Everaerts, F. M., J. L. Beckers, et al., published in Amsterdam and New York by Elsevier Scientific Pub. Co. in 1976, and hereby incorporated by reference in its entirety.

The simplest applications of ITP to controlling chemical reactions are enhancing the concentration of a reactant and using ITP to move a chemical reaction zone through a system. However, ITP also allows for control of several other significant aspects of chemical reactions, and it is these further aspects that are of interest here.

In a first aspect, at least one of the reactants of a chemical reaction is confined to an ITP zone, but the resulting product of the chemical reaction is separated from this ITP zone by the ITP process. This amounts to simultaneous reaction and separation operations, where a reaction takes place in the ITP zone, and the product is separated from this zone. The product can be unconfined by the ITP, or it can be confined by the ITP to a separate ITP zone than the reactant zone.

In a second aspect, one or more reactants of a chemical reaction are confined to an ITP zone, and one or more other reactants of the chemical reaction are not confined to this ITP zone. This amounts to a situation where the un-confined reactants can "flow through" the ITP zone where the reaction takes place. For example, a species with effective mobility higher than the LE can be injected in the TE reservoir. It will then electromigrate through the TE zone, through the sample zone(s), and finally through the LE zone in the channel and into the LE reservoir.

In a third aspect, ITP is employed to confine at least one reactant of a chemical reaction to an ITP zone, and at least one reactant of the chemical reaction is delivered to the ITP zone in two or more discrete doses.

All three of the above aspects are relevant to and offer substantial advantages in connection with a preferred embodiment where PCR is carried out using chemical denaturants. It is convenient to refer to such PCR reactions as chemically cycled PCR (ccPCR). The nucleic acids and primers/oligonucleotides of the PCR reaction are confined by ITP, while repeated doses of a nucleic acid denaturant flow through the ITP zone. In many cases, it is preferable to control the ITP zone motion so that it is substantially stationary relative to the walls of the liquid channel. This can be done by opposing the sample electromigration with a pressure-driven and/or electroosmosis-driven counter-flow of the solvent. This can be accomplished by matching the ITP migration velocity with an equal and opposite area-averaged velocity of the solvent (the bulk liquid) in the channel. Creating a substantially stationary ITP zone with respect to the lab can significantly simplify controlling the timing and method of injecting discrete reactant doses into the channel and the monitoring of concentrations of reactants and/or products, e.g., using fluorescent tags. Catalysts and/or enzymes can be provided in the ITP reaction zone in order to alter reaction rates, typically to effectively increase rates.

The ITP process may be able to simultaneously provide the PCR reaction and separation of PCR reaction constituents. For example, nucleic acid templates can be separated from oligonucleotides by confinement to two separate ITP zones. In some cases an electrophoretic spacer ion can be added that forms a separate ITP zone between the nucleic acid template zone and the oligonucleotide zone, thereby further enhancing the separation of PCR reaction constituents. Preferably, the PCR reaction is carried out at constant temperature, thereby avoiding the complexities associated with thermal cycling.

DETAILED DESCRIPTION

Definitions

The term "nucleic acid" as used herein means a polymer composed of nucleotides ("polynucleotides"), e.g., deoxyribonucleotides or ribonucleotides, or compounds produced synthetically which can hybridize with naturally occurring nucleic acids in a sequence specific manner analogous to that of two naturally occurring nucleic acids, e.g., can participate in Watson-Crick base pairing interactions. The terms "nucleic acid" and "polynucleotides" are used interchangeably.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" or "oligo" as used herein denotes single-stranded nucleotide multimers up to about 400 nucleotides in length.

Hybridization means the combination of complementary, single-stranded nucleic acids into a single molecule. "Hybridizing" and "binding" are used interchangeably.

"High" denaturant concentrations mean working concentrations of more than 10% v/v or more than 1 M.

"Low" denaturant concentrations mean working concentrations of ≤10% v/v or ≤1 M.

Figure 1:
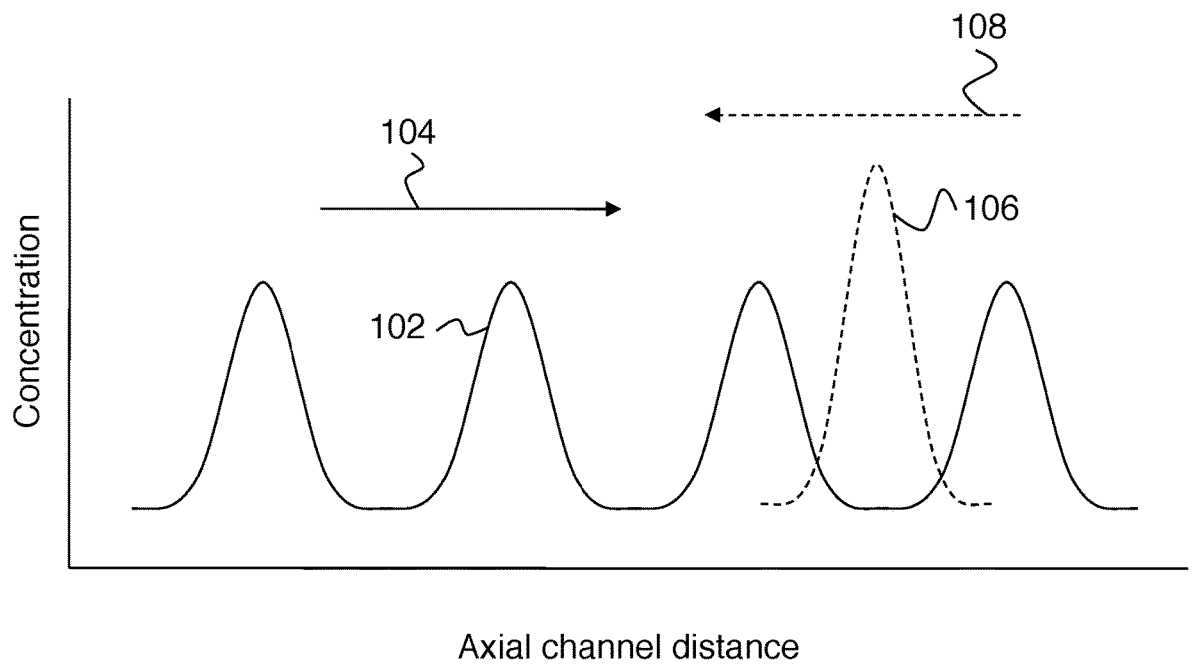
FIG. 1 illustrates a conceptual representation of chemical cycling PCR.

FIG. 1 is a conceptual representation of ccPCR. Clouds of high denaturant concentration (one of which is labeled as 102) flow in a direction 104. A DNA template 106 has an ITP electromigration direction 108 that is opposite to direction 104. As a result of this counter-flow process, template 106 experiences a chemical cycling that can mimic the denaturing and then annealing effects caused by thermal cycling in classical PCR. Locally high denaturant concentration regions melt double-stranded nucleic acid, while locally low denaturant regions allow for polynucleotide annealing and extension.

During the denaturation, annealing and enzyme-aided extension process, the nucleic acid can be kept stationary in a microfluidic channel by balancing flow velocity 104 with ITP velocity 108, while being exposed in a counter-flow stream to a series of individual clouds of moving denaturant. This exposes the nucleic acid to alternately high and low concentrations of denaturant. ITP provides focusing of the nucleic acids and protects the nucleic acids from being dispersed during amplification. The nucleic acid can remain stationary with respect to the laboratory frame of reference, while denaturant clouds move with the counter-flow.

The chemical cycling process can be facilitated through spatial fluctuations in the concentration of the chemical denaturants along a microchannel, which can be created by a flow control scheme, and results from the high electrophoretic mobility of nucleotides and the electrical neutrality of denaturants. Since denaturant clouds are electrically neutral, they are driven forward toward, through, and then away from the nucleic acid zone. The velocity of the nucleic acid zone can be greater or less than that of the "train" of denaturant clouds. The velocity of the nucleic acid zones can also be zero or non-zero relative to the laboratory frame. Preferably, the nucleic acid zone is substantially stationary with respect to the laboratory frame. The nucleic acid zone velocity is different than that of the denaturant clouds because of the electric field and the differing charge state of the denaturant and nucleic acid.

The enzyme used for extension of the primer can be a heat-labile polymerase or polymerase fragment (lacking 5'→3' exonuclease activity), e.g. Klenow fragment of DNA polymerase I, or a thermostable polymerase, e.g. Taq DNA polymerase. Chemical denaturants can be used in concentrations >10% to denature and open up double-stranded polynucleotides. Chemical denaturants can be used in concentrations of 0-10% to allow for and to adjust annealing and extension processes.

Polynucleotide samples can be kept stationary and confined using ITP, while moving electrokinetically through varying concentrations of chemical denaturants. The electromigration velocity of the nucleic acid can be balanced out by the application of a pressure-driven or electroosmosis-driven counter flow of denaturants clouds.

Several advantages follow from this approach. PCR amplification time can be significantly decreased. PCR system and supporting instrumentation design can be simplified (since no thermal cycling is required). PCR specificity and quantitative accuracy can be increased. PCR costs can be decreased. The tendency of the nucleic acid to be dispersed by the denaturant flow is counter-acted by the ITP process, which ensures stable confinement of the nucleic acids while allowing denaturant flow-through. Amplified products can simultaneously be separated by ITP while amplification is ongoing.

Figure 2:
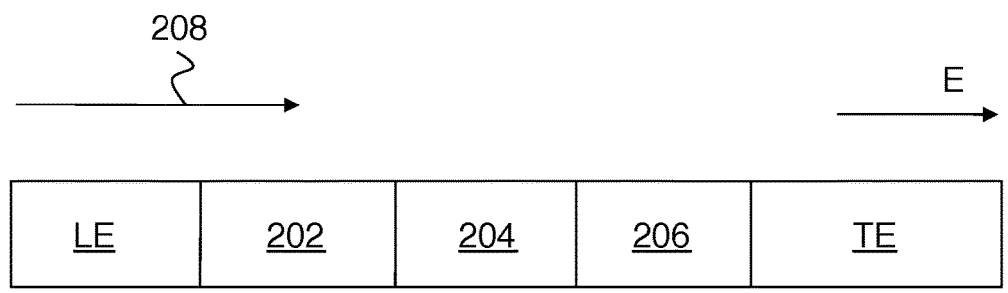
FIG. 2 illustrates the focusing of DNA with isotachophoresis in chemical cycling PCR conditions.

FIG. 2 shows an example of the focusing of DNA with isotachophoresis in ccPCR conditions. Here LE is the leading electrolyte, TE is the trailing electrolyte, 202 is the DNA template ITP zone, 206 is the oligonucleotide (primer) ITP zone, and 204 is the ITP zone of a non fluorescent spacer (here benzoate) that separates the DNA from the primers, providing PCR product localization. The use of a spacer as shown here can facilitate PCR product localization. The direction of the denaturant counter-flow in this example is shown as 208.

Figure 3A:
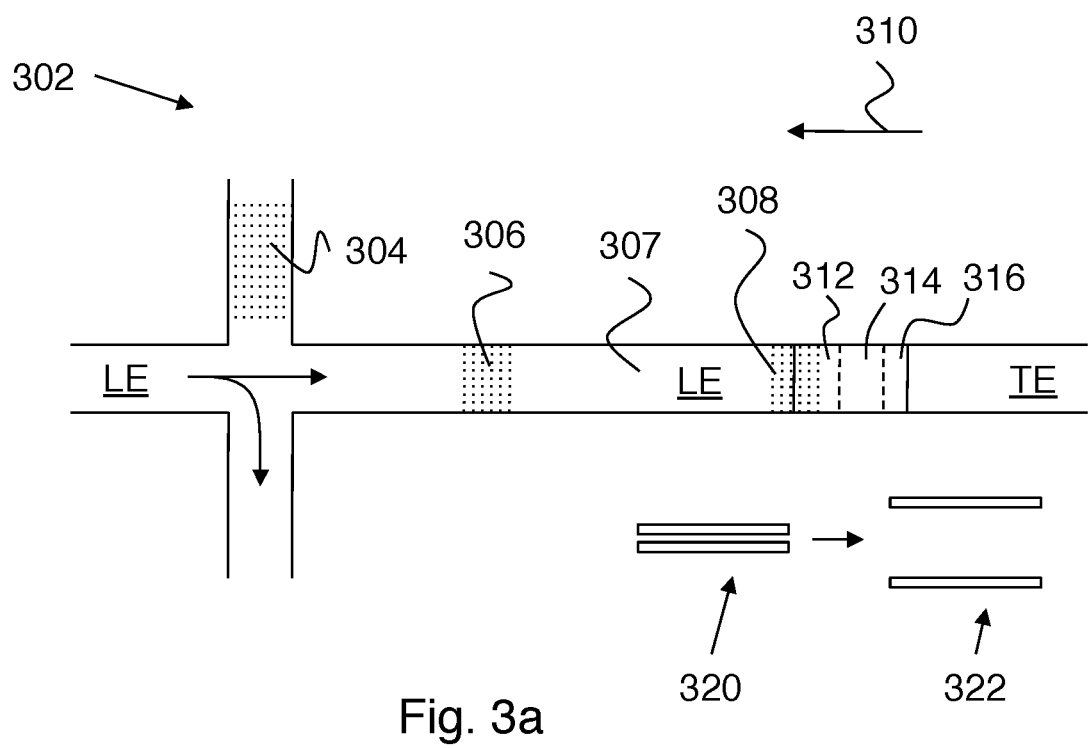
FIGS. 3a-b depict an exemplary method of on-chip chemical cycling PCR.
Figure 3B:
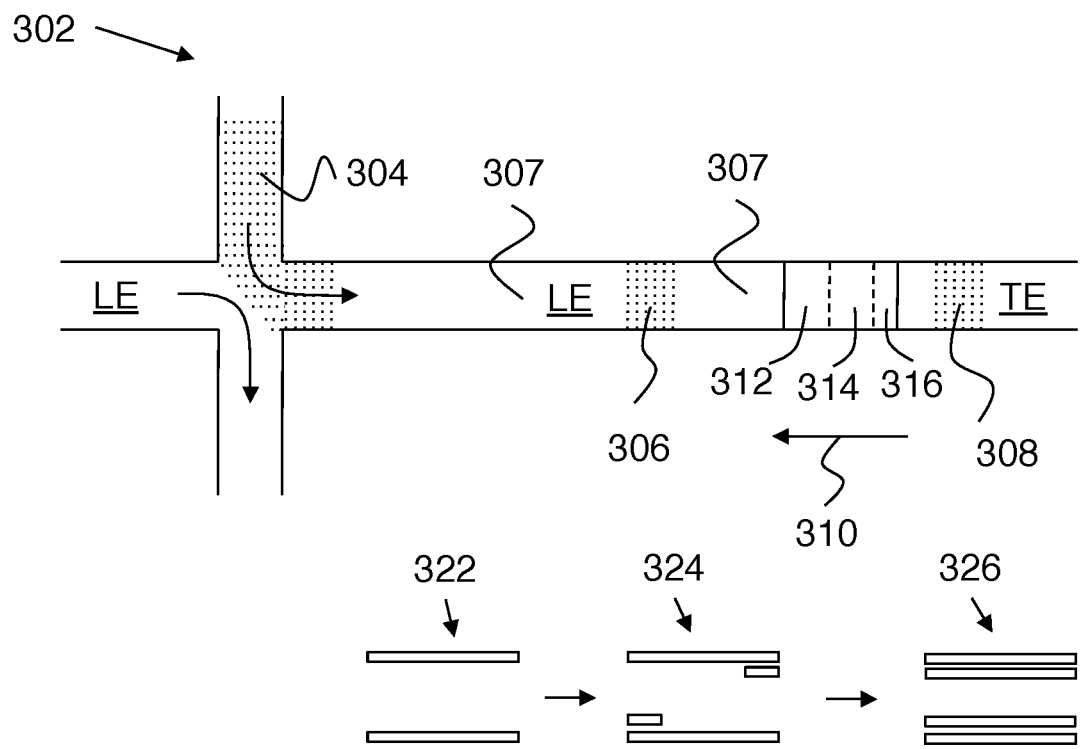

FIGS. 3a-b show an exemplary scheme of on-chip ccPCR in a cross channel 302. A DNA template zone 312 is confined by ITP between a leading electrolyte LE and a trailing electrolyte TE. A spacer zone 314 and a primer zone 316 are also confined by ITP between the LE and TE, as shown. The ITP velocity is shown as 310, and is opposite to the direction of fluid flow in the channel such that the ITP zones are roughly stationary with respect to the channel. Two consecutive denaturant clouds are shown as 306 and 308. They are separated by PCR buffer 307, which also includes the leading electrolyte and is accordingly labeled as LE. A flow control scheme at the cross using a denaturant reservoir 304 can be employed to provide these periodic clouds of denaturant.

The situation shown on FIG. 3a is when a cloud of denaturant (i.e., cloud 308) just enters the DNA template zone. The resulting reaction in the ITP zones is schematically shown as double stranded DNA 320 separating into its single strands 322. The situation shown on FIG. 3b is after cloud 308 has passed through the ITP zones. The resulting reaction in the ITP zones is schematically shown as single-stranded DNA 322 binding to a primer to provide primed DNA strands 324, which are then extended to corresponding double stranded DNA 326 by a polymerase.

A series of clouds (small controlled volumes, doses or "plugs") of chemical denaturants can be introduced into an amplification channel with a valve and pressure driven flow. During the denaturation, annealing and extension process, the nucleic acid is kept at a velocity different than that of the "train" of denaturant clouds on the microfluidic platform by an electric field. The nucleic acid is kept focused in a relatively small region (relative to channel length) by an electric field gradient that is achieved by isotachophoresis, while being exposed in a counter-flow stream to clouds of moving denaturants of alternately high and low concentrations. Locally high denaturant concentration regions melt the nucleic acid, while locally low denaturant regions allow for nucleic acid annealing and extension. The electric field aids to focus and refocus the nucleic acid and protects the nucleic acid from dispersing during amplification.

The chemical cycling process can be facilitated through spatial fluctuations in the concentration of the chemical denaturants along a microchannel, which can be created by a pressure-driven flow control scheme, and is achieved through the high electrophoretic mobility of nucleotides combined with the electrical neutrality of denaturants.

The DNA sample can be initially introduced into a channel section between the two electrolytes used in the isotachophoresis process. Upon application of the electric field, isotachophoresis focuses the sample into a sharp zone.

Denaturing chemical agents have the ability to reduce the melting temperature of DNA, i.e. the temperature at which double-stranded DNA separates into two complementary single strands. The chemical cycling PCR runs at a temperature at which DNA is single stranded in denaturant, but double stranded in regular buffer (with water only as solvent). High denaturant concentration allows denaturation, while low concentration allows annealing and extension. The denaturants used in one particular embodiment of the invention are formamide and urea. Any other compounds that can act as nucleic acid denaturants can also be employed.

Non thermostable polymerases such as the Klenow fragment from *E. Coli* DNA polymerase I have enhanced accuracy compared to thermostable polymerases. Also, the temperature at which their activity is optimum is close to typical room temperature. Chemical cycling in conjunction with non thermostable polymerase has the potential to perform DNA amplification at room temperature with high accuracy.

The denaturant injection can be controlled by pressure driven flow or electroosmotic flow. For pressure driven flow, denaturant and other buffers can be connected to the inlets of the chip with capillary tubing. Flow can be generated with a hydrostatic pressure head or an automated pressure controller. A valve allows switching off flow between buffer and denaturant. Periodic switching of the valve creates denaturant cycles within the channel. For electroosmotic injection, the chip wells can be filled with buffer and denaturant. Using a four output power supply, the flow can be controlled to create a succession of gated electroosmotic injections of denaturant, while keeping the direction of the electric field the same in the DNA channel throughout the experiment.

For applications of the present approach to PCR, the PCR buffers have to be compatible with isotachophoresis. Isotachophoresis leverages the difference of electrophoretic mobility of ions to create electric field gradients. Isotachophoresis buffers are not necessarily compatible with the PCR reaction. For PCR/ITP combinations that are untested, initial control experiments to verify compatibility should be performed.

In some cases, electroosmotic flow allows better control and reproducibility of the injection and reduced dispersion compared to pressure-driven counter-flow. In electroosmotic flow, the surface charge on the channel walls originates the flow upon application of an electric field in the channel.

In ccPCR, longer double-stranded nucleic acids can be continuously separated from primer-dimers and primers during the amplification reaction using an electrophoretic spacer (e.g., as shown on FIGS. 2 and 3a-b), while the fluorescence of the specific PCR product can be monitored for quantitation purposes. An electrophoretic spacer is an ionic species which has properties such that it ends up between the template and the primers in the ITP stack of zones.

Experiment 1: On-Chip Chemical Cycling Polymerase Chain Reaction Using Formamide and Urea as Denaturants This assay was performed in a simple cross borosilicate glass microchip (model NS95, Caliper, Mountain View, Calif.) coated with polyvinylpyrrolidone. Off-chip PCR buffer and denaturant reservoirs were connected to a low dead volume switching valve (model C2, Vici Valco, Houston, Tex.). The valve was connected to the chip with nanoports (Upchurch Scientific, Oak Harbor, Wash.) and fused silica capillaries (Upchurch Scientific, Oak Harbor, Wash.). The pressure head between the off-chip reservoirs and the chip drives the flow. The chip was on an electric heater maintained at 55° C. with a Peltier device and a temperature controller (Omega Engineering, Stamford, Conn.). A sourcemeter (model 2410, Keithley, Cleveland, Ohio) was used to apply high voltage and perform ITP.

The reaction was monitored with an inverted epifluorescent microscope (Eclipse TE300, Nikon) equipped with a cooled CCD camera (Princeton instruments, Trenton, N.J.), and controlled with the data acquisition software V++. Images were processed with MATLAB.

A 1×PCR Mastermix (Qiagen, Valencia, Calif.) was used as the leading electrolyte (LE). The Mastermix contains 50 mM potassium chloride, 10 mM Tris hydrochloride, 1.5 mM magnesium chloride, 2.5 U/100 μL Taq DNA polymerase, 200 μM of each dNTP. The trailing electrolyte was 25 mM Tris HEPES with 2.5 U/100 μL Taq DNA polymerase (Qiagen, Valencia, Calif.), 200 μM of each dNTP (New England Biolabs, Ipswich, Mass.), and 1.5 mM magnesium chloride. Both LE and TE contain 20 nM of forward and reverse primers (Operon, Huntsville, Ala.), 2 μM SYTO13 intercalating dye (Molecular Probes, Eugene, Oreg.) and 0.01% Tween 20 (Sigma, St Louis, Mo.). The denaturant was 40% formamide 4M urea buffered with 1×PCR buffer and containing 1.5 mM magnesium chloride, 2 μM SYTO13 and 20 nM of each primer. The DNA template (194 bp segment 341-534 of the 16S rRNA gene from $E.\ Coli.$) was diluted in LE solution.

A finite amount of DNA template was initially injected hydrodynamically between LE and TE. Then, a voltage was applied to start ITP focusing. Once the template was focused, the voltage was adjusted so that the sample remains stationary in its channel. Then the denaturant cycling was started by actuating the denaturant valve. SYTO13 fluorescence was monitored during the denaturant cycles.

Figure 4:
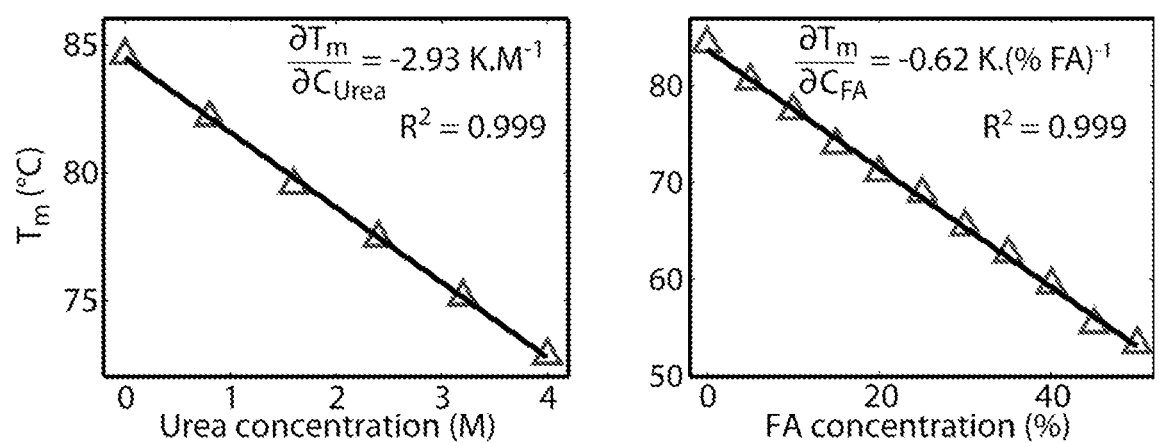
FIG. 4 illustrates the correlation of solvent type and concentration with nucleotide melting temperature using the example of 16S rRNA.

FIG. 4 illustrates the correlation of solvent type and concentration with nucleotide melting temperature using the example of 16S rRNA. Measured effect of formamide and urea concentration on melting temperature $T_m$ of the 16S rRNA gene from $E.\ Coli.$ $T_m$ decreases with increasing urea and formamide concentrations. These results demonstrate the effect of formamide and urea as denaturants.

Figure 5A:
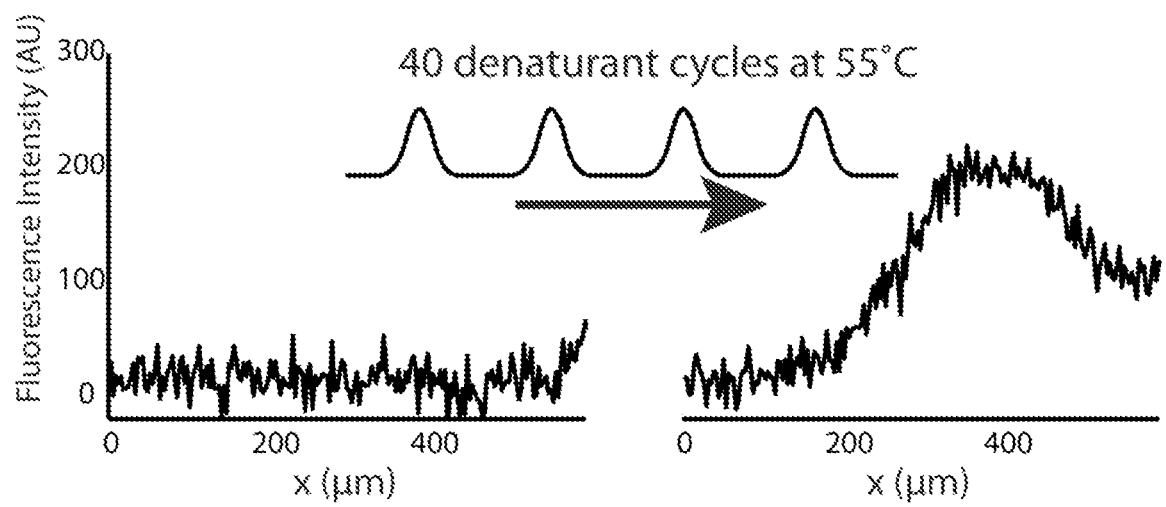
FIGS. 5a-5b illustrate end-point detection and real-time monitoring of chemical cycling PCR.
Figure 5B:
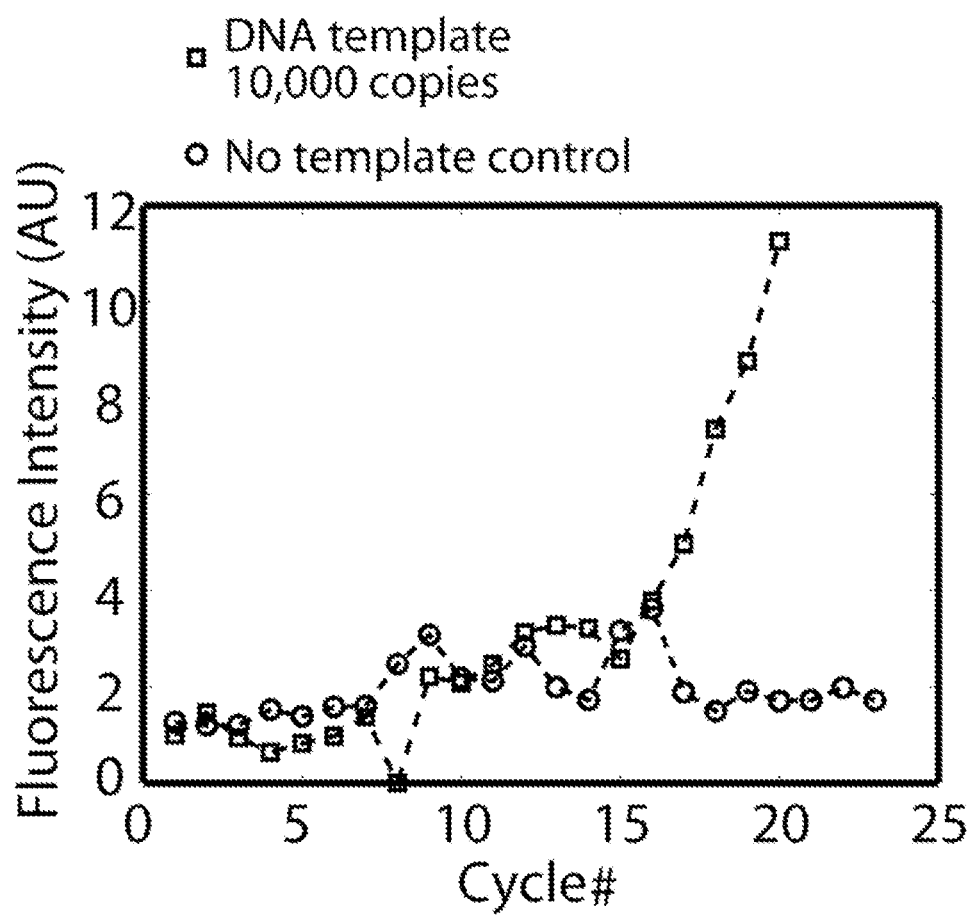

FIGS. 5$a$-5$b$ illustrate end-point detection and real-time monitoring of ccPCR. a) Isotachopherograms of PCR product zone before (left) and after 40 ccPCR cycles (right). This type of end point detection allows identification of DNA sequences of interest. b) Real time fluorescence monitoring of ccPCR. Initially, the PCR product fluorescence signal is below limit of detection.

Experiment 2: Initial PCR/ITP Control Experiments

A series of calibration experiments were performed to optimize the chemistry and flow conditions. The efficacy of Taq Polymerase was demonstrated for a relatively low extension temperature of 55° C. Final concentrations of three-step classical PCR products of a 200 bp template from $E.\ coli$ by agarose gel electrophoresis were compared. The PCR trials show very similar yields for extension temperatures of 55° C. and 72° C. demonstrating high Taq activity at 55° C. for the tested template (data not shown). This result shows that annealing and extension are possible at 55° C.

In a second set of experiments, it was verified that the ITP conditions can result in a buffer compatible with PCR. Buffer type, buffer concentration, and DNA concentration can have a strong effect on PCR efficiency. Ionic concentration was varied by changing the PCR buffer concentration of a three-step classical PCR from 1× to 6× (1×PCR buffer corresponds to 50 mM KCl, 20 mM Tris-HCl) and PCR yields for each concentration were compared by agarose gel electrophoresis. PCR yield decreases dramatically for buffer concentrations greater than about 3× (data not shown). Similar experiments suggest that PCRs in Tris-HEPES buffer with concentrations ranging from 25 mM to 100 mM have similar yields to PCR in a 1×PCR buffer (data not shown).

A counter flow stream with alternately high and low denaturant concentration was moved through ITP-confined polynucleotide samples, as in FIG. 3. The counter-flow stream can be pressure driven and/or electroosmotic. Double-stranded DNA (dsDNA) concentration was monitored via SYBR Green I intercalating dye fluorescence and single-stranded DNA (ssDNA) concentration was monitored by SYBR Green II fluorescence. A fused silica microchip with silanized channels was employed, and Tween 20 was added to all solutions to minimize protein adsorption.

Figure 6:
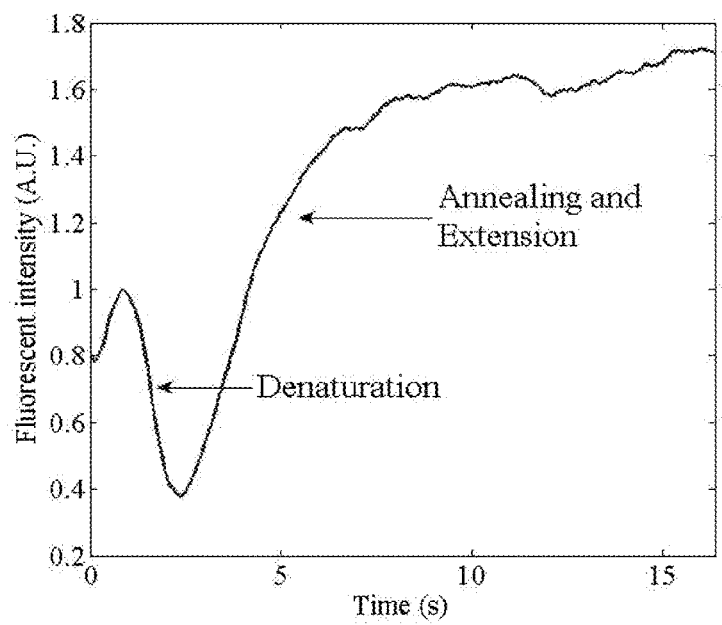
FIG. 6 shows monitored DNA concentration results from an experiment.

FIG. 6 is a plot of DNA concentration monitored via SYBR Green I fluorescence plotted versus time. Under conditions of balanced electromigration and bulk flow velocity, the DNA plug oscillates within about a 1 mm region. Fluorescent intensity decreases dramatically during denaturing before increasing as DNA amplifies via annealing and extension.

Figure 7:
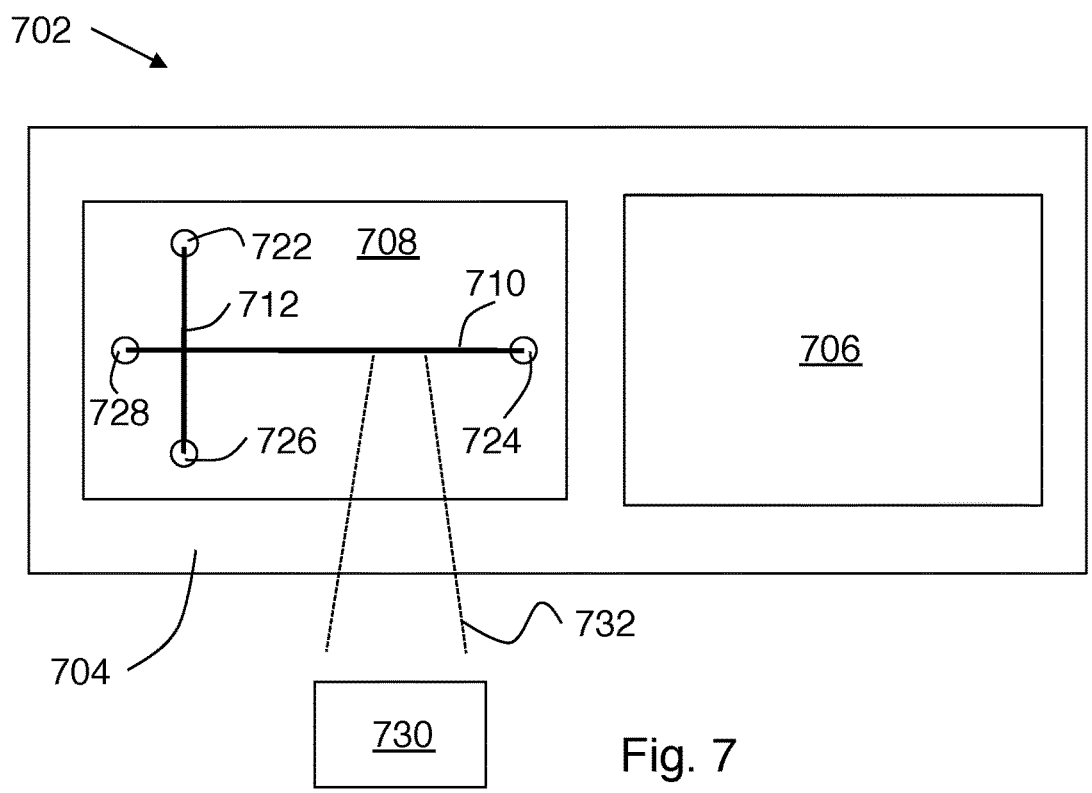
FIG. 7 shows an example of suitable apparatus for practicing some embodiments of the invention.

FIG. 7 shows an example of a device 702 suitable for practicing the above-described ITP/PCR process. A microfluidic chip 708 having crossed channels 710 and 712 sits on a plate 704 maintained at a constant temperature of 55° C. at which denaturant activity is optimum. The temperature of plate 704 can be maintained by a Peltier device 706 attached to a heat sink (not shown). Electric field can be applied from HV well 724 to GND well 726 to effect ITP focusing of DNA. PCR buffer flows continuously into chip PCR well 728 via hydrostatic pressure. Denaturant flows into well 722 under control by a valve (not shown) that is actuated in pulses causing small denaturant injection clouds to flow toward the HV well. Voltage is preferably controlled to hold the DNA band approximately stationary via ITP dynamics. The chemical concentration cycling amplification process can monitored in real time by measuring intensity of fluorescence 732 at the end of each amplification cycle with a monitor 730. Real time fluorescence monitoring can be performed with an epifluorescent microscope and a computer controlled CCD camera. ccPCR product quantity can be determined by intercalating dye fluorescent or by sequence specific fluorescent probe such as molecular beacons.

The preceding description has been by way of example as opposed to limitation, and various modifications of the given examples also rely on the above-described principles. In particular, the preceding examples relate to the various chemical processes associated with the polymerase chain reaction. However, the use of ITP to control chemical reactions can be applied to any chemical reaction, not just PCR. The preceding examples also relate to the use of micro-fluidic devices. However, standard capillaries and interconnects can also be employed.

The invention claimed is:

1. An isotachophoresis (ITP) apparatus comprising:
   at least a first liquid flow channel containing:
   a) a leading electrolyte;
   b) a trailing electrolyte;
   c) a catalyst, an enzyme, or a denaturant; and
   d) a nucleic acid;

wherein said first liquid flow channel is in liquid communication with at least a first reservoir, a second reservoir, or a third reservoir, wherein:
i) if present, said first reservoir comprises said leading electrolyte;
ii) if present, said second reservoir comprises said trailing electrolyte; or
iii) if present, said third reservoir comprises said catalyst, enzyme, or denaturant.

2. The apparatus of claim 1, wherein said first liquid flow channel comprises a second liquid flow channel connected to a third liquid flow channel wherein said second liquid flow channel comprises said leading electrolyte and said third liquid flow channel comprises said trailing electrolyte.

3. The apparatus of claim 2, further comprising a reservoir fluidly coupled to said first, second, or third liquid flow channels.

4. The apparatus of claim 1, wherein said nucleic acid comprises a deoxyribonucleic acid.

5. The apparatus of claim 4, wherein said deoxyribonucleic acid is double-stranded.

6. The apparatus of claim 4, wherein said deoxyribonucleic acid is single-stranded.

7. The apparatus of claim 1, wherein said first liquid flow channel further comprises a ribonucleic acid.

8. The apparatus of claim 1, wherein said first liquid flow channel further comprises at least one primer, oligonucleotide, or dNTP.

9. The apparatus of claim 1, wherein said first liquid flow channel further comprises a confined nucleic acid template.

10. The apparatus of claim 1, wherein said first liquid flow channel further comprises a confined oligonucleotide.

11. The apparatus of claim 1, wherein said first liquid flow channel further comprises an electrophoretic spacer ion.

12. The apparatus of claim 1, wherein said first liquid flow channel further comprises a fluorescent dye, an intercalating fluorescent dye, a sequence specific fluorescent probe, or a molecular beacon.

13. The apparatus of claim 1, wherein said first liquid flow channel further comprises SYBR Green I, SYTO 13, or SYBR Green II.

14. The apparatus of claim 1, wherein said catalyst, enzyme, or denaturant comprises a denaturant.

15. The apparatus of claim 14, wherein said denaturant comprises a nucleic acid denaturant.

16. The apparatus of claim 1, wherein said catalyst, enzyme, or denaturant comprises an enzyme.

17. The apparatus of claim 16, wherein said enzyme is a polymerase.

18. The apparatus of claim 17, wherein said polymerase is a thermostable DNA polymerase, a heat-labile polymerase, a non-thermostable polymerase, or a polymerase fragment.

19. The apparatus of claim 17, wherein said polymerase comprises a Klenow fragment of DNA polymerase I or a Taq DNA polymerase.

20. The apparatus of claim 1, wherein said apparatus is configured to be coupled to a system for monitoring a concentration of at least one of a reactant or a product in said first liquid flow channel.

21. The apparatus of claim 1, wherein said apparatus is coupled to a fluorescence detector.

22. The apparatus of claim 1, wherein said apparatus is coupled to a heater.

23. The apparatus of claim 1, wherein said apparatus is coupled to a temperature controller.

24. The apparatus of claim 1, wherein said reservoir is a first reservoir comprising said first reservoir and said second reservoir are both present, wherein said first reservoir comprises said leading electrolyte, and wherein said second reservoir comprises said trailing electrolyte.

25. The apparatus of claim 24, wherein said third reservoir is present and wherein said third reservoir comprises said catalyst, enzyme, or denaturant.

26. An isotachophoresis (ITP) apparatus comprising:
at least a first liquid flow channel containing:
a) a leading electrolyte,
b) a trailing electrolyte,
c) a catalyst, an enzyme, or a denaturant, and
d) a nucleic acid,
wherein said first liquid flow channel comprises a second liquid flow channel connected to a third liquid flow channel wherein said second liquid flow channel comprises said leading electrolyte and said third liquid flow channel comprises said trailing electrolyte; and
a reservoir fluidly coupled to said first, second, or third liquid flow channels.

27. An isotachophoresis (ITP) apparatus comprising:
at least a first liquid flow channel containing:
a) a leading electrolyte,
b) a trailing electrolyte,
c) a catalyst, an enzyme, or a denaturant, and
d) a ribonucleic acid.

28. An isotachophoresis (ITP) apparatus comprising:
at least a first liquid flow channel containing:
i. a leading electrolyte;
ii. a trailing electrolyte; and
iii. a denaturant, wherein said denaturant comprises urea or formamide; and
iv. a nucleic acid.

29. An isotachophoresis (ITP) apparatus comprising at least a first liquid flow channel comprising:
(a) a first zone comprising a trailing electrolyte buffer comprising a trailing electrolyte;
(b) a second zone comprising a sample comprising an analyte, wherein said analyte comprises a ribonucleic acid;
(c) a third zone comprising a leading electrolyte buffer comprising a leading electrolyte that is faster than said trailing electrolyte; and
(d) a catalyst, enzyme, or denaturant,
wherein said analyte has an electrophoretic mobility between said trailing electrolyte and said leading electrolyte, and
wherein said catalyst, enzyme, or denaturant, is (i) positioned ahead of said analyte if said catalyst, enzyme, or denaturant, has an electrophoretic mobility slower than said electrophoretic mobility of said analyte; or (ii) positioned behind said analyte if said catalyst, enzyme, or denaturant, has an electrophoretic mobility faster than said electrophoretic mobility of said analyte.

30. The apparatus of claim 29, wherein said leading electrolyte buffer comprises said catalyst or enzyme.

31. The apparatus of claim 29, wherein said first liquid flow channel further comprises at least one primer, oligonucleotide, or dNTP.

32. The apparatus of claim 29, wherein said catalyst, enzyme, or denaturant comprises a denaturant.

33. The apparatus of claim 29, wherein said catalyst, enzyme, or denaturant comprises an enzyme.

34. The apparatus of claim 29, wherein said catalyst, enzyme, or denaturant comprises a catalyst.

\* \* \* \* \*